(12) United States Patent
Kanazawa et al.

(10) Patent No.: US 6,326,360 B1
(45) Date of Patent: Dec. 4, 2001

(54) BUBBLING ENTERIC COATED PREPARATIONS

(75) Inventors: Hashime Kanazawa; Kenji Shimizu; Kazuhiro Sasaki; Tetsuya Sugimoto, all of Tokyo (JP)

(73) Assignee: Grelan Pharmaceuticals Co., Ltd., Tokyo (JP)

(*) Notice: Subject to any disclaimer, the term of this patent is extended or adjusted under 35 U.S.C. 154(b) by 0 days.

(21) Appl. No.: 09/623,706

(22) PCT Filed: Mar. 10, 1999

(86) PCT No.: PCT/JP99/01157
§ 371 Date: Sep. 25, 2000
§ 102(e) Date: Sep. 25, 2000

(87) PCT Pub. No.: WO99/45934
PCT Pub. Date: Sep. 16, 1999

(30) Foreign Application Priority Data

Mar. 11, 1998 (JP) ................................................. 10-076487

(51) Int. Cl.[7] ........................ A61K 31/715; A61K 31/70; A61K 9/46; A61K 9/20; A61K 9/28
(52) U.S. Cl. ........................ 514/53; 514/572; 514/33; 514/25; 424/466; 424/465; 424/468; 424/474
(58) Field of Search ................................ 514/572, 53, 33, 514/25; 424/466, 474, 468, 464, 465, 43, 44

(56) References Cited

U.S. PATENT DOCUMENTS

| | | | |
|---|---|---|---|
| 3,961,041 | 6/1976 | Nishimura et al. | 424/35 |
| 4,687,662 * | 8/1987 | Schobel | 424/44 |
| 4,835,142 | 5/1989 | Suzuki et al. | 514/53 |
| 5,498,425 * | 3/1996 | Wood et al. | 424/464 |
| 5,567,439 * | 10/1996 | Myers et al. | 424/486 |

FOREIGN PATENT DOCUMENTS

| | | |
|---|---|---|
| 51-57813 | 5/1976 | (JP) . |
| 3-255037 | 11/1991 | (JP) . |
| 6-192107 | 7/1994 | (JP) . |
| 7-277972 | 10/1995 | (JP) . |

* cited by examiner

Primary Examiner—Zohreh Fay
Assistant Examiner—Brian-Yong Kwon
(74) Attorney, Agent, or Firm—Wenderoth, Lind & Ponack, L.L.P.

(57) ABSTRACT

An object of the present invention is to obtain an oral glycyrrhizin preparation not only manufacturable by a simple method but also having an excellent property of being absorbed from the digestive tract. In the present invention, such oral preparations are made into enteric forms wherein glycyrrhizin is admixed with an effervescent agent in combination with an absorption enhancer such as a medium-chain fatty acid or a salt thereof. In the preparation of the present invention, it is now possible to achieve an excellent absorption of glycyrrhizin from the digestive tract by addition of an effervescent agent and, moreover, the preparation can be manufactured by a simple, convenient method without special steps.

8 Claims, No Drawings

BUBBLING ENTERIC COATED PREPARATIONS

This is a 371 application of PCT/JP99/01157 filed Mar. 10, 1999.

TECHNICAL FIELD

The present invention relates to an oral pharmaceutical preparation for glycyrrhizin (which is also called glycyrrhizic acid or glycyrrhizinic acid; referred herein to as "glycyrrhizin") having the good property of being well absorbed from the digestive tract. More particularly, the present invention relates to an effervescent enteric pharmaceutical preparation thereof.

BACKGROUND ART

Glycyrrhizin is a pharmaceutically active ingredient which is appreciated as a therapeutic agent for hepatic diseases and for allergy, and a medically essential drug due to its excellent improving action for hepatic functions, especially in the therapy of chronic hepatic diseases. At present, two kinds of clinically used glycyrrhizin-containing preparations, i.e., injection preparations and oral tablets, are available. In view of efficacy, the use of injection preparations is overwhelming. In the case of tablets, it has been reported that glycyrrhizin is quickly decomposed into glycyrrhetinic acid in the stomach, that transfer of unchanged glycyrrhizin having a high pharmacological activity into blood is hardly observed and accordingly that its effect is far poor as compared with injection preparations (Minophagen Medical Review, Extra Issue No.30, page 1 (1993)).

However, in the case of injection preparations, a dosage level for each administration is as high as 40–100 ml. It compels pain to the patient and, moreover, causes a lot of burden including hospitalization for long time or necessity of visiting the hospital for injection every day or several days a week to the patient in the case of chronic hepatic diseases requiring a therapy for a long period. Therefore, the use of suppositories or oral preparations as substitutes for injection preparations has been proposed where the improvement of absorption is attempted.

For instance, there have been proposals for suppositories, such as a suppository where a conventionally known base such as Witepsol H-15 is used (JP, 1-294619, A (1989)), a suppository where at least one kind of nonionic surface-active agents or medium-chain fatty acids is admixed as an absorption enhancer (JP, 4-261117, A (1992)) and a suppository where a nonionic surface-active agent is admixed, as an absorption enhancer, with an oleaginous base (JP, 5-97680, A (1993)). For oral preparations with an object of improvement in absorption, the following has been proposed: a preparation where fatty acid glyceride is admixed followed by coating with an enteric film (JP, 3-255037, A (1991)) and a preparation where glycyrrhizin is made into a fat emulsion, a mixture with a conjugated lipid, or dry powders thereof (JP, 6-192107, A (1994)).

However, those conventional preparations have disadvantages as described hereinbelow.

For the above-mentioned suppositories, it takes a long therapeutic term to treat chronic hepatic diseases as mentioned already, and the use of suppositories for a long period therefore compels a considerable burden on the patient although it will not be so much as in the case of injection preparations.

Further, for the above-mentioned oral preparations, the prior art example as disclosed in JP, 3-255037, A (1991) is discussed because the prior art oral preparation is administered to rats intraduodenally instead of orally in which glycyrrhizin is merely dispersed in a fatty acid glyceride mixture and consequently the concentration of glycyrrhizin in blood is measured whereby there are no data which scientifically and clearly support the oral efficacy of the disclosed preparation.

For the next prior art example as disclosed in JP, 6-192107, A (1994), a fat emulsion or conjugated lipid mixture of glycyrrhizin is prepared therein. Unlike solid preparations such as tablets, however, such a liquid preparation inherently has an anxiety of stability and its handling is also inconvenient. Even if such an emulsified preparation is dried and made into powders, steps for manufacturing such a preparation are quite complicated.

As such, at the level of the conventional art, it is difficult to prepare an oral preparation of glycyrrhizin causing little burden to patients and having the excellent property of being well absorbed from the digestive tract.

DISCLOSURE OF THE INVENTION

Under such circumstances, the present inventors have carried out an intensive study for the manufacture of oral glycyrrhizin preparations manufacturable by a simple, convenient method and exerting the property of being excellently well absorbed from the digestive tract. As a result, the present inventors have found that such problems can be solved when an oral preparation is made into an enteric form wherein glycyrrhizin is admixed with not only an absorption enhancer but also an effervescent agent. Based on their further investigation, they have succeeded in completing the present invention.

Thus, the present invention provides:

(1) an oral pharmaceutical preparation comprising glycyrrhizin or a pharmaceutically acceptable salt thereof, an absorption enhancer and an effervescent agent;

(2) the oral pharmaceutical preparation according to the above (1), which is enteric;

(3) the preparation according to the above (1) or (2), wherein the absorption enhancer is a $C_6$ to $C_{20}$ fatty acid or a salt thereof;

(4) the preparation according to the above (1) or (2), wherein the absorption enhancer is a medium-chain fatty acid or a salt thereof;

(5) the preparation according to the above (1) or (2), wherein the absorption enhancer is capric acid or a salt thereof;

(6) the preparation according to the above (1) or (2), wherein the absorption enhancer is a medium-chain fatty acid glyceride; and (7) the preparation according to the above (1) or (2), wherein the effervescent agent consists of sodium hydrogen carbonate and citric acid or tartaric acid.

In another aspect, the present invention provides:

(8) the preparation according to the above (1) or (2), wherein the absorption enhancer is an alkyl ester of fatty acid;

(9) the preparation according to the above (1) or (2), wherein the absorption enhancer is a nonionic surface-active agent;

(10) the preparation according to the above (1) or (2), wherein the absorption enhancer is a bile acid salt;

(11) the preparation according to the above (1) or (2), wherein the absorption enhancer is a nonsteroidal anti-inflammatory agent;

(12) the preparation according to any of the above (1) to (3), wherein the absorption enhancer is selected from the group consisting of caproic acid, caprylic acid, capric acid, lauric acid, myristic acid, palmitic acid, stearic acid, isostearic acid, oleic acid, linoleic acid and linolenic acid as well as sodium salts, potassium salts and calcium salts thereof;

(13) the preparation according to any of the above (1) to (4), wherein the absorption enhancer is a $C_6$ to $C_{12}$ fatty acid or a salt thereof;

(14) the preparation according to any of the above (1) to (4) and (13), wherein the absorption enhancer is selected from the group consisting of caproic acid, caprylic acid, capric acid and lauric acid as well as sodium salts, potassium salts and calcium salts thereof;

(15) the preparation according to any of the above (1), (2) or (6), wherein the absorption enhancer is selected from the group consisting of mono-, di- and/or tri-glycerides of $C_6$ to $C_{12}$ fatty acids;

(16) the preparation according to any of the above (1), (2), (6) or (15), wherein the absorption enhancer is selected from the group consisting of mono-, di- and/or tri-glycerides of a compound selected from the group consisting of caproic acid, caprylic acid, capric acid and lauric acid;

(17) the preparation according to any of the above (1) to (6) and (8) to (16), wherein the effervescent agent is a substance which has a property of, when the administered preparation is dissolved or disintegrated in the digestive tract, producing a gaseous substance such as carbon dioxide gas to disperse the drug, etc.;

(18) the preparation according to any of the above (1) to (6) and (8) to (17), wherein the effervescent agent is a couple comprising one or more organic acids in combination with one or more basic substances; and

(19) the preparation according to any of the above (1) to (6) and (8) to (18), wherein the effervescent agent is a couple comprising (A) one or more organic substances selected from the group consisting of citric acid (including citric anhydride), tartaric acid and phthalic acid in combination with (B) one or more basic substances selected from the group consisting of salts of carbonic acid with alkaline metals and alkaline earth metals, including sodium hydrogen carbonate, potassium hydrogen carbonate, sodium carbonate, potassium carbonate, magnesium carbonate and the like.

In still another aspect, the present invention provides:

(20) an enteric preparation containing glycyrrhizin or a pharmaceutically acceptable salt, an absorption enhancer and an effervescent agent;

(21) the preparation according to any of the above (1) to (20), wherein the preparation is selected from the group consisting of tablets, granules, powders, pulverized drugs, hard capsules and soft capsules;

(22) the preparation according to any of the above (1) to (21), wherein the preparation is coated with an enteric coating base;

(23) the preparation according to any of the above (1) to (20), wherein the preparation is selected from the group consisting of hard capsules and soft capsules wherein each capsule contains an enteric coating base in its shell;

(24) an oral preparation comprising glycyrrhizin or a pharmaceutically acceptable salt thereof, said oral preparation being characterized in that the preparation exerts, by oral administration, an excellent blood level profile of unchanged glycyrrhizin or a substantially equal property thereto;

(25) the preparation according to the above (24), wherein the blood level profile of unchanged glycyrrhizin is as represented by Table 7 or exerts a property in the similar mode thereto;

(26) the preparation according to the above (24) or (25), wherein the blood level profile of unchanged glycyrrhizin is effective in view of a therapeutic agent for hepatic diseases or as a therapeutic agent for allergy;

(27) the preparation according to the above (24) or (25), wherein the blood level profile of unchanged glycyrrhizin is effective for the therapy of chronic hepatic diseases;

(28) an oral preparation comprising glycyrrhizin or a pharmaceutically acceptable salt thereof, said oral preparation being characterized in that the preparation exerts, by oral administration, an excellent pharmacokinetic parameter concerning the transfer of unchanged glycyrrhizin into blood or a substantially equal property thereto;

(29) the preparation according to the above (28), wherein at least one of the pharmacokinetic parameters concerning the transfer of unchanged glycyrrhizin into blood is any of representatives in Table 8 or exerts a property in the similar mode thereto;

(30) the preparation according to the above (28) or (29), wherein at least one of the pharmacokinetic parameters concerning the transfer of unchanged glycyrrhizin into blood is an effective level in view of an agent for hepatic diseases or an agent for allergy;

(31) the preparation according to the above (28) or (29), wherein at least one of the pharmacokinetic parameters concerning the transfer of unchanged glycyrrhizin into blood is an effective level for the therapy of chronic hepatic diseases; and

(32) an oral preparation containing glycyrrhizin or a pharmaceutically acceptable salt thereof, said oral preparation being characterized in providing, via oral administration, the bioavailability effective as a therapeutic agent for hepatic diseases, such as a therapeutic agent for chronic hepatic diseases and a therapeutic agent for allergy.

The above objects and other objects, features, advantages, and aspects of the present invention are readily apparent to those skilled in the art from the following disclosures. It should be understood, however, that the description of the specification, including the following best modes for carrying out the invention, examples, test examples, etc., is illustrating preferred embodiments of the present invention and given only for explanation thereof. It will become apparent to the skilled in the art that a great number of variations and/or alterations (or modifications) of this invention may be made based on knowledge from the disclosure in the following parts and other parts of the specification without departing from the spirit and scope thereof as disclosed herein. All of the patent publications and reference documents cited herein for illustrative purposes are hereby incorporated by reference into the present disclosure.

The term "and/or" used herein means the presence of both (1) a jointly connecting relation and (2) a selectively connecting relation. For example, in the case of "di- and/or tri-glycerides", it is used in such a sense that said expression covers both (1) "di-glycerides and tri-glycerides" and (2) "di-glycerides or tri-glycerides". In other cases, the term "and/or" is used in such a sense that it covers both (1) a jointly connecting relation and (2) a selectively connecting relation as well.

BEST MODE FOR CARRYING OUT THE INVENTION

Specific embodiments of the present invention are oral pharmaceutical glycyrrhizin preparations, particularly effervescent enteric glycyrrhizin preparations, having an excellent property of being well absorbed from the digestive tract. Further preferred embodiments of the present invention are as follows:

(A) an oral pharmaceutical preparation and an enteric preparation, comprising glycyrrhizin or a pharmaceutically acceptable salt thereof, an absorption enhancer and an effervescent agent;

(B) the preparation according to the above (A), wherein the absorption enhancer is a $C_6$ to $C_{20}$ fatty acid or a salt thereof;

(C) the preparation according to the above (A), wherein the absorption enhancer is a medium-chain fatty acid or a salt thereof;

(D) the preparation according to the above (A), wherein the absorption enhancer is capric acid or a salt thereof;

(E) the preparation according to the above (A), wherein the absorption enhancer is a medium-chain fatty acid glyceride; and (F) the preparation according to the above (A), wherein the effervescent agent consists of sodium hydrogen carbonate and citric acid or tartaric acid.

The above-mentioned "glycyrrhizin and a pharmaceutically acceptable salt thereof" refers to glycyrrhizin, mono- or di-ammonium salts of glycyrrhizin, mono- or di-sodium salts of glycyrrhizin, mono- or di-potassium salts of glycyrrhizin, etc. In the present invention, each of them may be used either alone or in combination with one or more other species thereof.

The above-mentioned absorption enhancer includes substances which are safe in vivo and have an action of giving a certain action to biomembranes being absorbing sites of the digestive tract to improve the permeability of a pharmaceutically active ingredient through the membrane. The absorption enhancer which is appropriately selected includes substances per se, in an amount used as an absorption enhancer, having no particular pharmacological action and having no interaction with a pharmaceutically active ingredient and with other additives. Specific examples of the said absorption enhancer are:

a) $C_6$ to $C_{20}$ fatty acids or salts thereof;
b) medium-chain fatty acids or salts thereof;
c) medium-chain fatty acid glycerides;
d) fatty acid alkyl esters;
e) nonionic surface-active agents;
f) bile acid salts;
g) nonsteroidal anti-inflammatory agents; and the like.

More specific examples of the above a) to g) are as follows:

a) $C_6$ to $C_{20}$ fatty acids or salts thereof: caproic acid, caprylic acid, capric acid, lauric acid, myristic acid, palmitic acid, stearic acid, isostearic acid, oleic acid, linoleic acid and linolenic acid; or sodium salts, potassium salts and calcium salts thereof;

b) medium-chain fatty acids or salts thereof: $C_6$ to $C_{12}$ fatty acids such as caproic acid, caprylic acid, capric acid and lauric acid; or sodium salts, potassium salts and calcium salts thereof;

c) medium-chain fatty acid glycerides: mono-, di- and/or tri-glycerides of $C_6$ to $C_{12}$ fatty acids such as caproic acid, caprylic acid, capric acid and lauric acid;

d) fatty acid alkyl esters: alkyl esters (such as methyl esters, ethyl esters, n-propyl esters, isopropyl esters, n-butyl esters, cetyl esters and isocetyl esters) of $C_6$ to $C_{20}$ fatty acids such as caproic acid, caprylic acid, capric acid, lauric acid, myristic acid, palmitic acid, stearic acid, isostearic acid, oleic acid, linoleic acid and linolenic acid; and dialkyl esters (such as dimethyl esters, diethyl esters, di-n-propyl esters and diisopropyl esters) of di-fatty acids such as sebacic acid and adipic acid;

e) nonionic surface-active agents: polyoxyethylene alkyl ethers (such as polyoxyethylene cetyl ether, polyoxyethylene lauryl ether, polyoxyethylene oleyl ether and polyoxyethylene stearyl ether), polyoxyethylene alkylaryl ethers (such as polyoxyethylene nonylphenyl ether), polyethylene glycol fatty acid esters (such as polyethylene glycol monostearate and polyethylene glycol distearate), sorbitan fatty acid esters (such as sorbitan sesquioleate, sorbitan trioleate, sorbitan monooleate, sorbitan monostearate, sorbitan monopalmitate and sorbitan monolaurate), propylene glycol fatty acid esters (such as propylene glycol dioleate and propylene glycol monostearate), polyoxyethylene hydrogenated castor oils (such as polyoxyethylene hydrogenated castor oil 50 and polyoxyethylene hydrogenated castor oil 60), polyoxyethylene sorbitan fatty acid esters (such as polyoxyethylene sorbitan monopalmitate, polyoxyethylene sorbitan monostearate, polyoxyethylene sorbitan monooleate and polyoxyethylene sorbitan monolaurate), glycerol fatty acid esters (such as glycerol monooleate and glycerol monostearate) and polyoxyethylene polyoxypropylene glycols;

f) bile acid salts: sodium deoxycholate, sodium taurodeoxycholate, sodium kenodeoxycholate, sodium glycoursocholate and sodium ursodeoxycholate; and g) nonsteroidal anti-inflammatory agents: sodium salicylate, sodium 5-methoxysalicylate and indomethacin.

Each of the above-mentioned absorption enhancers may be used either alone or in combination with one or more other species thereof. Among them, the particularly preferred absorption enhancers are the above-mentioned medium-chain fatty acid or a salt thereof, medium-chain fatty acid glyceride, etc.

The above-mentioned effervescent agent includes substances having a property of, when the administered preparation is dissolved or disintegrated in digestive tract, producing gaseous substances (carbon dioxide gas) to disperse (or release) the drug, etc. Representative examples of the effervescent agent are couples each comprising one or more organic acids in combination with one or more basic substances. The organic acid includes citric acid (including citric anhydride), tartaric acid and phthalic acid, etc. The basic substance includes salts of carbonic acid with alkaline metals and alkaline earth metals (carbonates including bicarbonates of alkaline metals and alkaline earth metals), such as sodium hydrogen carbonate, potassium hydrogen carbonate, sodium carbonate, potassium carbonate and magnesium carbonate.

The above-mentioned absorption enhancer and effervescent agent are used and made into a pharmaceutical preparation by a known method per se to give a desired preparation (such as tablets, granules, powders, pulverized drugs, hard capsules and soft capsules) and, at that time, it is preferred to carry out a treatment for an enteric preparation. The above enteric preparation means tablets, granules, powders, pulverized drugs for oral use coated with an enteric coating base and hard and soft capsules using capsules coated with an enteric coating base with an object that the preparation is not disintegrated in the stomach but is integrated in the intestine. Specific examples of the substance which is used as the said enteric coating base are hydroxypropyl methyl cellulose phthalate, hydroxypropyl methyl cellulose acetate succinate, carboxymethyl ethyl cellulose, cellulose acetate phthalate, copolymers of methacrylic acid with ethyl acrylate, copolymers of methacrylic acid with methyl methacrylate, cellulose acetate trimellitate, polyvinyl acetate phthalate and shellac. Each of those enteric coating bases may be used either alone or in combination with one or more other species thereof in an appropriate manner.

In addition to the above-mentioned absorption enhancer and effervescent agent, other pharmaceutically compatible ingredients may be added as the ingredients which are used in the oral preparation of the present invention. In some cases, that is rather preferred for achieving the object of the present invention. Examples of such additional ingredients are various amino acids such as aminoacetic acid, L-cysteine and DL-methionine and salts thereof (such as hydrochlorides and alkaline metal salts).

The oral preparation of the present invention can be manufactured by common methods for the manufacture of tablets, granules, powders, pulverized drugs and capsules such as a method mentioned in General Rules for Preparations in the Japanese Pharmacopoeia (the 13th Revision) and by a known method which is commonly used in coating by an enteric coating base. In that case, in addition to the above-mentioned absorption enhancer and effervescent agent, it is, as desired, possible to admix fillers, binders, lubricants, stabilizers, corrigents, coloring agents, etc. which are commonly used in the manufacture of pharmaceutical preparations.

The amount of glycyrrhizin or a pharmaceutically acceptable salt thereof contained in the oral preparation of the present invention may be a level such that desired pharmaceutical efficacy can be achieved. Although it may vary depending upon symptom, age, body weight, etc. of the patient, the amount as estimated in terms of glycyrrhizin is about 1 to 1,000 mg per administration, which may be administered once or by several times a day.

The amount of the absorption enhancer contained in the oral preparation of the present invention may be a level such that it is sufficient to achieve the object of enhancing absorption. It is usually about 0.1 to 30 parts by weight, or preferably about 0.2 to 20 parts by weight, to one part by weight of glycyrrhizin. An amount of the effervescent agent contained in the oral preparation of the present invention is about 0.1 to 20 parts by weight, or preferably about 0.2 to 10 parts by weight, to one part by weight of glycyrrhizin. An amount of the enteric coating base in the enteric preparation of the present invention may be a level such that it is sufficient not to cause a disintegration in the stomach. An enteric coating of about 50 to 500 microns is usually applied to the outside of the oral preparation (such as tablet) according to the present invention. Alternatively, conventional enteric hard or soft capsules may be used as they are. The use of such capsules is rather convenient.

In the preparation of the present invention, an art of adding absorption enhancers thereto and enteric coating is adopted for improving the absorption of glycyrrhizin from the digestive tract. In addition, effervescent agents are used herein which have not been attempted so far at all. As a result, absorption of glycyrrhizin from the intestine is achieved whereby a practical oral preparation of glycyrrhizin has been accomplished for the first time. Thus, after the enteric coating is dissolved in the small intestine, the preparation contacts with the liquid in the intestine and, together with effervescence, glycyrrhizin is released simultaneously. The fact that the said effervescent stage greatly contributes to a delivery of unchanged glycyrrhizin into blood has been presumed and ascertained by the biological test which will be mentioned hereinbelow.

EXAMPLES

Described below are examples, including comparative examples and test examples, of the present invention which are provided only for illustrative purposes, and not to limit the scope of the present invention. It should be understood that, in the present invention, various embodiments based upon the spirit of the present specification are feasible. All the examples, including comparative examples and test examples, were or can be practiced using standard techniques well or conventionally known to those of ordinary skill in the art unless otherwise specified.

Example 1

Ingredients for core tablet formulations as listed in Table 1 (Example 1) were mixed and the resulting powder for tableting was directly compressed into tablets (each tablet having about 9.0 mm diameter and about 5 mm thickness) using a tableting machine. The resulting tablets were further subjected to an enteric coating step using hydroxypropyl methyl cellulose acetate succinate (HPMCAS) which was a coating ingredient for the formulation.

TABLE 1

Ingredients for Formulations per one Tablet

|  | Ingredients for Formulations | Example 1 (mg) (Tablet) | Comparative Example 1 (mg) (Tablet*) |
|---|---|---|---|
| Core Tablet | Glycyrrhizin | 40.0 | 40.0 |
|  | Citric anhydride | 39.0 | 39.0 |
|  | Sodium hydrogen carbonate | 51.0 | 51.0 |
|  | Crystalline cellulose | 49.3 | 69.3 |
|  | Corn starch | 49.2 | 69.2 |
|  | Crospovidone | 15.0 | 15.0 |
|  | Synthetic aluminum silicate | 15.0 | 15.0 |
|  | Magnesium stearate | 1.5 | 1.5 |
|  | Sodium caprate | 40.0 | — |
| Coating | HPMCAS | 30.0 | 30.0 |
|  | Total | 330.0 | 330.0 |

*Effervescent enteric-coated tablets containing no absorption enhancer

Comparative Example 1

Ingredients for formulations as listed in Table 1 (Comparative Example 1) (using no sodium caprate) were treated in the same manner as in Example 1 to obtain enteric-coated tablets.

Examples 2 to 4

Each formulation containing ingredients as listed in Table 2 (Examples 2 to 4, respectively) was treated in the same manner as in Example 1 to obtain enteric-coated tablets.

TABLE 2

Ingredients for Formulations per one Tablet

| | Ingredients for Formulations | Example 2 (mg) (Tablet) | Example 3 (mg) (Tablet) | Example 4 (mg) (Tablet) |
|---|---|---|---|---|
| Core Tablet | Glycyrrhizin | 40.0 | 40.0 | 40.0 |
| | Citric anhydride | 39.0 | 39.0 | — |
| | Tartaric acid | — | — | 42.5 |
| | Sodium hydrogen carbonate | 51.0 | 51.0 | 47.5 |
| | Crystalline cellulose | 60.0 | 39.5 | 80.0 |
| | Lactose | 60.0 | 39.0 | 40.0 |
| | Crospovidone | 15.0 | — | — |
| | Agar | — | 15.0 | 15.0 |
| | Synthetic aluminum silicate | 15.0 | 15.0 | 15.0 |
| | Magnesium stearate | — | 1.5 | — |
| | Sodium laurate | 20.0 | — | — |
| | Sodium oleate | — | 60.0 | — |
| | Sodium caprate | — | — | 20.0 |
| Coating | HPMCAS | 30.0 | 30.0 | 30.0 |
| | Total | 330.0 | 330.0 | 330.0 |

Examples 5 and 6

Each powder composition obtained by mixing ingredients for Example 5 and 6 formulations, respectively, as listed in Table 3 was filled in commercially available enteric capsules AS-L (trade name; manufactured by Freund Sangyo KK) #0 and #3 to obtain enteric capsule preparations.

TABLE 3

Ingredients for Formulations per one Capsule

| Ingredients for Formulations | Example 5 (mg) (Capsule) | Example 6 (mg) (Capsule) |
|---|---|---|
| Glycyrrhizin | 40.0 | 40.0 |
| Citric anhydride | 39.0 | 19.0 |
| Sodium hydrogen carbonate | 51.0 | 25.0 |
| Crystalline cellulose | 65.0 | — |
| Corn starch | 65.0 | — |
| Sodium caprate | 40.0 | 40.0 |
| Total | 300.0 | 124.0 |
| Remark | filled in enteric capsule | filled in enteric capsule |

Example 7

Ingredients except HPMCAS for formulations as listed in Table 4 (Example 7) were mixed, and the resulting powder was granulated using an extruding granulator. The products were sized into spherical granules with an uniform size of about 1.2 mm diameter and enteric-coated using HPMCAS with a centrifugal fluidizing type coating apparatus to obtain enteric granules.

TABLE 4

Ingredients for Granule Formulations

| Ingredients for Formulations | Example 7 (mg) (Granules) |
|---|---|
| Glycyrrhizin | 40.0 |
| Tartaric acid | 21.2 |
| Sodium hydrogen carbonate | 23.8 |
| Crystalline cellulose | 120.0 |
| Lactose | 40.0 |
| Corn starch | 25.0 |
| Low-substituted hydroxypropyl cellulose | 20.0 |
| Sodium caprate | 20.0 |
| HPMCAS | 90.0 |
| Total | 330.0 |

Comparative Example 2

Ingredients for formulations as listed in Table 5 (Comparative Example 2) were filled in capsules AS-L #0 as aforementioned to manufacture an enteric capsule preparation containing neither absorption enhancer nor effervescent agent.

Comparative Example 3

Capric acid was added to glycyrrhizin for formulations as listed in Table 5 (Comparative Example 3), homogeneously suspended and filled in the same enteric capsule as in Comparative Example 2 to manufacture an enteric capsule preparation containing no effervescent agent.

TABLE 5

Ingredients for Formulations per one Capsule

| Ingredients for Formulations | Comparative Example 2 (mg) (Capsule*[1]) | Comparative Example 3 (mg) (Capsule*[2]) |
|---|---|---|
| Glycyrrhizin | 40 | 40 |
| Capric acid | — | 460 |
| Remark | filled in enteric capsule | filled in enteric capsule |

*[1]containing neither absorption enhancer nor effervescent agent
*[2]containing no effervescent agent

Comparative Example 4

Ingredients for formulations as listed in Table 6 (Comparative Example 4) were treated in the same manner as in Example 1 to manufacture an enteric-coated tablet containing no effervescent agent.

TABLE 6

Ingredients for Formulations per one Tablet

| Ingredients for Formulations | Comparative Example 4 (mg) (Tablet) |
|---|---|
| Glycyrrhizin | 40.0 |
| Crystalline cellulose | 94.2 |
| Corn starch | 94.3 |
| Crospovidone | 30.0 |
| Magnesium stearate | 1.5 |
| Sodium caprate | 40.0 |
| HPMCAS | 30.0 |
| Total | 330.0 |

Test Example 1

<Test Method>

Effervescent enteric-coated tablets manufactured in Example 1 and Comparative Example 1 were orally administered to beagles (male; body weight: 10–12 kg, each group consisting of three dogs) at a dosage rate of 1 tablet (containing 40 mg of glycyrrhizin) per beagle, respectively. Blood was collected with certain intervals of time and the blood concentration of glycyrrhizin in an unchanged form was measured by means of a high performance liquid chromatography. Table 7 shows the resulting blood level profiles. Thereafter, C max (maximum blood level), T max (time required for arriving the maximum blood level) and AUC (area under the concentration-time curve) during 10 hours after the administration were determined and shown in Table 8. All data shown in Tables 7 and 8 are the average of three beagles each.

TABLE 7

Blood Level of Unchanged Glycyrrhizin

| Time Elapsed after Administration (hour(s)) | Preparations of Example 1 (Tablets) (µg/ml) | Preparations of Comparative Example 1 (Tablets) (µg/ml) |
|---|---|---|
| 0 | 0.0 | 0.0 |
| 0.5 | 0.0 | 0.0 |
| 1.0 | 0.0 | 0.0 |
| 2.0 | 0.0 | 0.0 |
| 3.0 | 7.16 | 0.36 |
| 4.0 | 7.22 | 0.35 |
| 6.0 | 4.86 | 0.28 |
| 8.0 | 3.97 | 0.26 |
| 10.0 | 3.60 | 0.24 |
| Remark | — | containing no absorption enhancer |

TABLE 8

Pharmacokinetic Parameters for Transfer of Unchanged Glycyrrhizin into Blood

| | Preparations of Example (Tablets) | Preparations of Comparative Example 1 (Tablets) | Preparations of Comparative Example 2 (Capsules) | Preparations of Comparative Example 3 (Capsules) | Preparations of Comparative Example 4 (Tablets) |
|---|---|---|---|---|---|
| $C_{max}$ (µg/ml) | 9.78 | 0.37 | undetectable | 1.72 | 0.42 |
| $T_{max}$ (hours) | 3.3 | 3.3 | undetectable | 4.0 | 6.7 |
| $AUC_{0-10}$ (µg · hr/ml) | 39.3 | 2.2 | undetectable | 10.8 | 1.7 |
| Relative ratio of AUC | 100 | 5.6 | — | 27.5 | 4.3 |
| Remark | — | containing no absorption enhancer | containing neither effervescent agent nor absorption enhancer | containing no effervescent agent | containing no effervescent agent |

<Result>

Both Example 1 and Comparative Example 1 are effervescent enteric-coated tablets. It is apparent from Tables 7 and 8 that the blood concentration of unchanged glycyrrhizin from 3rd to 10th hr after the administration was within as low as 0.24 to 0.36 µg/ml in the case of Comparative Example 1 preparations containing no absorption enhancer (sodium caprate) while, in the case of Example 1 preparations, it was within as high as 3.60 to 7.22 µg/ml whereby it was ascertained that the preparation of the present invention showed an excellent property of enhancing the absorption of glycyrrhizin.

Test Example 2

<Test Method>

Enteric capsule preparations manufactured in Comparative Examples 2 and 3 were orally administered to beagles (male; body weight: 10–12 kg, each group consisting of three dogs) at a dosage rate of 1 capsule (containing 40 mg of glycyrrhizin) per beagle, respectively. Blood was collected with certain intervals of time and the blood concentration of glycyrrhizin in an unchanged form was measured by means of a high performance liquid chromatography. Table 9 shows the resulting blood level profiles. Thereafter, C max, T max and AUC during 10 hours after the administration were determined and shown in Table 8. All data shown in Tables 8 and 9 are the average of three beagles each.

TABLE 9

Blood Level of Unchanged Glycyrrhizin

| Time Elapsed after Administration (hour(s)) | Preparations of Comparative Example 2 (Capsules) (µg/ml) | Preparations of Comparative Example 3 (Capsules) (µg/ml) |
|---|---|---|
| 0 | 0.0 | 0.0 |
| 0.5 | 0.0 | 0.0 |
| 1.0 | 0.0 | 1.01 |
| 2.0 | 0.0 | 1.02 |
| 4.0 | 0.0 | 1.51 |
| 6.0 | 0.0 | 1.23 |
| 8.0 | 0.0 | 1.05 |
| 10.0 | 0.0 | 0.10 |
| Remark | containing neither effervescent agent nor absorption enhancer | containing no effervescent agent |

<Result>

Both Comparative Example 2 and 3 preparations are enteric capsule preparations each containing no effervescent agent. It is apparent from Tables 8 and 9 that unchanged glycyrrhizin was not detected in blood in the case of Comparative Example 2 preparations containing neither effervescent agent nor absorption enhancer while the blood concentrations of glycyrrhizin were within a range of 0.10 to 1.51 µg/ml from 1st to 10th hr after the administration in the case of Comparative Example 3 preparations containing absorption enhancers, showing some absorption enhancing effects. However, it is apparent that the Comparative Example 3 preparation showed lower absorption enhancing effects for glycyrrhizin than the Example 1 preparation containing effervescent agents in combination with absorption enhancers.

Test Example 3

<Test Method>

Enteric-coated tablets manufactured in Comparative Example 4 were orally administered to beagles (male; body weight: 10–12 kg, each group consisting of three dogs) at a dosage rate of 1 tablet (containing 40 mg of glycyrrhizin) per beagle. Blood was collected with certain intervals of time and the blood concentration of glycyrrhizin in an unchanged form was measured by means of a high performance liquid chromatography. From the said blood level profile, C max, T max and AUC during 10 hours after the administration were determined and shown in Table 8. All data shown in Table 8 are the average of three beagles each.

<Result>

The Comparative Example 4 preparation was an enteric-coated tablet containing absorption enhancers but no effervescent agent. It is apparent from Table 8 that the maximum blood level of unchanged glycyrrhizin was as low as 0.42 $\mu$g/ml and that, as compared with the Example 1 preparation containing both absorption enhancers and effervescent agents, the effect for enhancing the absorption of glycyrrhizin was very low.

Industrial Applicability of the Invention

In accordance with the present invention, the effervescent enteric preparations of glycyrrhizin can facilitate a more excellent absorption of glycyrrhizin from the digestive tract by admixture with effervescent agents, as compared with the conventional oral pharmaceutical preparations with an attempt to improve absorption. In addition, the said inventive preparations can be manufactured by a simple, convenient method without special steps whereby they are advantageous in view of the manufacture of pharmaceutical preparations. The present invention provides practically useful oral glycyrrhizin preparations resulting in little burden to patients and exerting the same good effect as the injection preparation.

While the present invention has been described specifically in detail with reference to certain embodiments, examples and biological test examples thereof, it would be apparent that it is possible to practice it in other forms. In light of the disclosure, it will be understood that various modifications and variations are within the spirit and scope of the appended claims.

What is claimed is:

1. An oral pharmaceutical preparation which consists essentially of glycyrrhizin or a pharmaceutically acceptable salt thereof as a pharmaceutically active agent, an absorption enhancer, which is a $C_6$ to $C_{20}$ fatty acid or a salt thereof, and an effervescent agent.

2. The oral pharmaceutical preparation according to claim 1, which is enteric-coated.

3. The preparation according to claim 1, wherein the absorption enhancer is a medium-chain fatty acid or a salt thereof.

4. The preparation according to claim 1, wherein the absorption enhancer is capric acid or a salt thereof.

5. The preparation according to claim 1, wherein the effervescent agent consists of sodium hydrogen carbonate and citric acid or tartaric acid.

6. The preparation according to claim 2, wherein the absorption enhancer is a medium-chain fatty acid or a salt thereof.

7. The preparation according to claim 2, wherein the absorption enhancer is capric acid or a salt thereof.

8. The preparation according to claim 2, wherein the effervescent agent consists of sodium hydrogen carbonate and citric acid or tartaric acid.

* * * * *